United States Patent [19]

Lösel et al.

[11] Patent Number: 5,614,516

[45] Date of Patent: Mar. 25, 1997

[54] 12-AMINOPYRIDAZINOPYRROLOISO-QUINOLINE COMPOUNDS

[75] Inventors: Walter Lösel, Gau-Algesheim; Otto Roos, Schwabenheim; Gerd Schorrenberg, Gau-Algesheim; Helmut Ensinger, Wackernheim; Richard Reichl, Gau-Algesheim, all of Germany

[73] Assignee: Boehringer Ingelheim GmbH, Ingelheim am Rhein, Germany

[21] Appl. No.: 384,902

[22] Filed: Feb. 7, 1995

Related U.S. Application Data

[63] Continuation of Ser. No. 294,460, Aug. 23, 1994, abandoned, which is a continuation of Ser. No. 151,081, Nov. 12, 1993, abandoned, which is a continuation of Ser. No. 26,675, Mar. 4, 1993, abandoned, which is a continuation of Ser. No. 912,049, Jul. 9, 1992, abandoned, which is a continuation of Ser. No. 779,208, Oct. 18, 1991, abandoned, which is a continuation of Ser. No. 668,347, Mar. 11, 1991, abandoned, which is a continuation of Ser. No. 549,657, Jul. 9, 1990, abandoned, which is a continuation of Ser. No. 432,932, Nov. 7, 1989, abandoned, which is a continuation of Ser. No. 322,325, Mar. 10, 1989, abandoned, which is a continuation of Ser. No. 196,905, May 20, 1988, abandoned, which is a continuation of Ser. No. 73,032, Jul. 14, 1987, abandoned, which is a continuation of Ser. No. 818,562, Jan. 13, 1986, abandoned.

[30] Foreign Application Priority Data

Jan. 1, 1985 [DE] Germany .................................. 3500941
Jul. 13, 1985 [DE] Germany .................................. 3525048

[51] Int. Cl.⁶ .................... C07D 487/04; A61K 31/50; A61K 31/535
[52] U.S. Cl. ................ 514/233.2; 514/247; 544/115; 544/233; 546/94
[58] Field of Search ............................ 544/233, 115; 514/248, 233.2

[56] References Cited

U.S. PATENT DOCUMENTS

| | | | |
|---|---|---|---|
| 4,508,720 | 4/1985 | Kan et al. | 544/224 |
| 4,694,085 | 9/1987 | Losel et al. | 544/233 |
| 4,721,711 | 1/1988 | Chambon et al. | 514/248 |

FOREIGN PATENT DOCUMENTS

| | | |
|---|---|---|
| 1288703 | 7/1954 | European Pat. Off. . |
| 73161 | 3/1983 | European Pat. Off. . |

OTHER PUBLICATIONS

Ferrari et al, *Chemical Abstracts*, vol. 71, No. 81215 (1969).
Losel et al, *Chemische Berichte*, 118, p. 413 (1985).

*Primary Examiner*—Emily Bernhardt
*Attorney, Agent, or Firm*—Robert P. Raymond; Alan R. Stempel; Mary-Ellen M. Devlin

[57] ABSTRACT

The invention relates to new 12-amino-pyridazino-[4',5':3,4]-pyrrolo[2,1-a]isoquinolines of general formula (I)

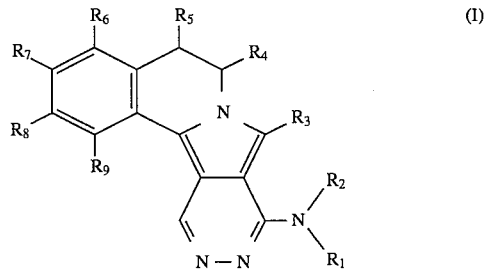

wherein $-NR_1R_2$ represents an amino or substituted amino group, and acid addition salts thereof. The new active substances have potential use in pharmaceutical compositions for treating cardiac insufficiency and cerebral metabolic disorders.

8 Claims, No Drawings

12-AMINOPYRIDAZINOPYRROLOISO-QUINOLINE COMPOUNDS

This is a continuation of Ser. No. 294,460, filed Aug. 23, 1994, now abandoned, which is a continuation of application Ser. No. 151,081, filed Nov. 12, 1993, now abandoned, which is a continuation of application Ser. No. 026,675, filed Mar. 4, 1993, now abandoned, which is a continuation of application Ser. No. 912,049, filed Jul. 9, 1992, now abandoned, which is a continuation of application Ser. No. 779,208, filed Oct. 18, 1991, now abandoned, which is a continuation of application Ser. No. 668,347, filed Mar. 11, 1991, now abandoned, which is a continuation of application Ser. No. 549,657, filed Jul. 9, 1990, now abandoned, which is a continuation of application Ser. No. 432,932, filed Nov. 7, 1989, now abandoned, which is a continuation of application Ser. No. 322,325, filed Mar. 10, 1989, now abandoned, which is a continuation of application Ser. No. 196,905, filed May 20, 1988, now abandoned, which is a continuation of application Ser. No. 073,032, filed Jul. 14, 1987, now abandoned, which is a continuation of application Ser. No. 818,562, filed Jan. 13, 1986, now abandoned.

The invention relates to new 12-amino-pyridazino-[4',5':3,4]pyrrolo[2,1-a]isoquinoline compounds. The new compounds are useful as agents for the treatment of cardiac and cerebral disorders.

According to one aspect of the invention, we provide compounds of formula

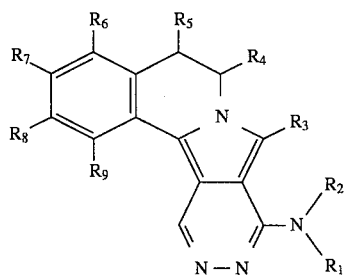

(I)

and the acid addition salts, especially the physiologically acceptable salts thereof wherein $R_1$ and $R_2$ are the same or different and each is hydrogen; $C_{3-7}$ cycloalkyl; $C_{2-5}$ alkenyl; phenyl; phenyl mono- or disubstituted by halogen or methoxy; propargyl; straight or branched chain, saturated or unsaturated $C_{1-5}$ alkyl which may be substituted by hydroxy, $C_{1-4}$ alkoxy, halogen, amino, $C_{1-2}$ alkylamino, $C_{1-2}$ dialkylamino, $C_{2-4}$ acylamino, $C_{3-7}$ cycloalkyl, phenyl or phenyl which is in turn substituted by halogen $C_{1-2}$ alkyl, $C_{1-2}$ alkoxy, amino. $C_{1-2}$ alkylamino, $C_{1-2}$ dialkylamino, $C_{2-3}$ acylamino, or alkysulphonylamino; furyl; thienyl; or, a nitrogen-containing heterocyclic 5- or 6-membered ring which may optionally contain an oxygen or sulphur atom as a further heteroatom and wherein the ring may optionally be substituted by a $C_{1-4}$ alkyl group:

or $R_1$ and $R_2$ together with the nitrogen atom to which they are attached form a 3- to 7-membered ring which may optionally contain an oxygen or nitrogen atom as a further heteroatom, the ring optionally being substituted by phenyl $(C_{1-4})$ alkyl, and this phenyl ring in turn being optionally mono- or disubstituted by halogen or methoxy; with the proviso that, when $R_1$ is hydrogen, $R_2$ may additionally be amino, $C_{1-2}$ dialkylamino, acetonylamino, $C_{2-3}$ acylamino, $C_{1-3}$ alkylsulphonyl, $C_{1-3}$ alkoxycarbonyl, isopropylideneimino, or a heterocyclic 5- or 6-membered ring containing a nitrogen atom and optionally an oxygen, nitrogen or sulphur atom as a further heteroatom;

$R_3$, $R_4$ and $R_5$ may be the same or different and each is hydrogen or $C_{1-4}$ alkyl $R_7$ and $R_8$ may be the same or different and each is hydroxy, $C_{1-4}$ alkoxy or $C_{1-4}$ alkylthio, and $R_6$ and $R_9$ may be the same or different and each is hydrogen, hydroxy, $C_{1-4}$ alkoxy, $C_{1-4}$ alkylthio, or a group

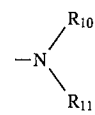

wherein $R_{10}$ is hydrogen or $C_{1-4}$ alkyl and $R_{11}$ is hydrogen or $C_{1-4}$ alkyl, any such alkyl group being optionally substituted by a hydroxy, methoxy or furfuryl group.

The invention also includes the pharmaceutically acceptable acid addition salts of the compounds of formula (I).

Preferred compounds are compounds of formula I or acid addition salts thereof in which $R_1$ and $R_2$, which may be the same or different, represent hydrogen atoms or a straight-or branched-chain $C_{1-5}$ alkyl group or $R_1$ represents a hydrogen atom and $R_2$ represents an amino, methylamino, dimethylamino, isopropylideneimino, dimethyl amino-$C_{1-4}$-alkyl, methoxy-$C_{1-4}$-alkyl, cyclopropyl, cyclopentyl, cyclohexyl, dyclohexylmethyl, pyrazolyl, phenyl, p-halophenyl or phenylethyl group, any such phenyl ring being optionally mono- or disubstituted by a methoxy group, or $R_1$ and $R_2$ together with the nitrogen atom to which they are attached represent a morpholino ring or a piperazine ring and $R_7$ and $R_8$ represent methoxy.

According to a further aspect of the invention we provide a process for preparing compounds of formula (I) as defined above wherein a 3,4-dihydro-12-methylmercapto-pyridazino[4',5':3,4]pyrrolo[2,1-a]-isoquinoline of general formula

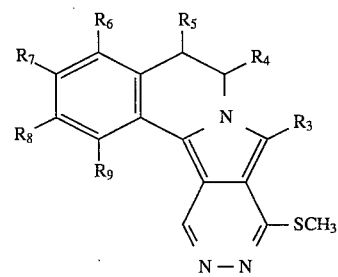

(II)

wherein the groups $R_3$, $R_4$, $R_5$, $R_6$, $R_7$, $R_8$ and $R_9$ are as hereinbefore defined, is reacted with a compound of general formula

(III)

wherein $R_1$ and $R_2$ are as hereinbefore defined.

In this reaction, a starting material of general formula (II) may be dissolved in a high-boiling inert solvent such as dimethylformamide, dimethylacetamide, chlorobenzene, hexamethylphosphorotriamide and refluxed with the amine compound of general formula (III) until the reaction is complete. The reaction time ranges from about 1 to 15 hours and will depend on the starting components used.

In the case of reactive amines, alcohols or tetrahydrofuran may also be used as solvent; under certain circumstances it may be advantageous to carry out the reaction in an autoclave.

If the amines used are liquid and sufficiently high-boiling, the reaction may also be carried out in an excess of the amine itself without any additional solvent, possibly under a nitrogen atmosphere. This may well be the situation when using aniline, morpholine, phenylethylamine.

In some cases it may also be possible and desirable to use a reaction partner which both serves as a solvent in the reaction and also yields the required amine by cleaving during the reaction, e.g. dimethylformamide.

The starting materials of general formula (II) may be prepared from a compound of general formula (IV)

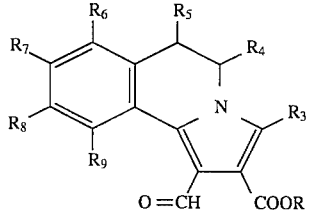

(IV)

wherein

R represents a $C_{1-4}$ alkyl group and the groups $R_3$, $R_4$, $R_5$, $R_6$, $R_7$, $R_8$ and $R_9$ are as hereinbefore defined, by reaction with hydrazine hydrate, and conversion of the resulting 3,4,11,12-tetrahydro-pyridazino[4',5':3,4]pyrrolo[2,1-a]isoquinolin-12-one of general formula (V)

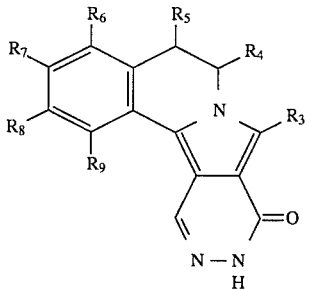

(V)

wherein the groups $R_3$, $R_4$, $R_5$, $R_6$, $R_7$, $R_8$ and $R_9$ are as hereinbefore defined, into the corresponding thione of general formula (VI)

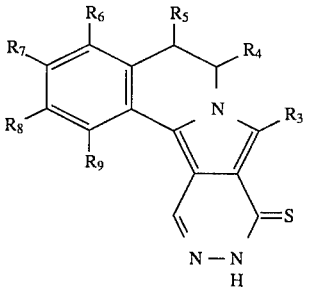

(VI)

wherein the groups $R_3$, $R_4$, $R_5$, $R_6$, $R_7$, $R_8$ and $R_9$ are as hereinbefore defined, using phosphorus pentasulphide followed by conversion of the thione compound formed into the corresponding methylmercapto compound of general formula (II)

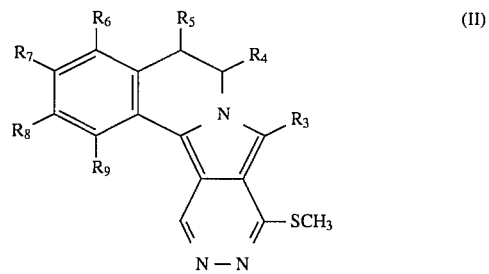

(II)

wherein the groups $R_3$, $R_4$, $R_5$, $R_6$, $R_7$, $R_8$ and $R_9$ are as hereinbefore defined, using a methylating agent such as dimethylacetamide/methyl iodide.

The starting materials of general formula IV may be obtained using the method described in German Patent Application P 34 01 018.1, now German Patent 3473455, and also U.S. Pat. No. 4,694,085, by base-catalyzed rearrangement of the 1-(3-furyl)-3,4-dihydroisoquinolines which are known from the literature.

The 12-amino-pyridazino-pyrazolo-isoquinolines according to the invention are bases and may be converted into acid addition salts, e.g. physiologically acceptable acid addition salts with inorganic or organic acids, in a conventional manner.

Acids suitable for salt formation include mineral acids, such as for example, hydrochloric, hydrobromic, hydriodic, hydrofluoric, sulphuric, phosphoric, and nitric acids or organic acids such as acetic, propionic, butyric, caproic, valeric, oxalic, malonic, succinic, maleic, fumaric, lactic, tartaric, citric, malic, benzoic, p-hydroxybenzoic, p-aminobenzoic, phthalic, cinnamic, salicylic, ascorbic and methanesulphonic acids.

Using the processes described hereinbefore, the following end products are readily obtained:

3,4-Dihydro-6,7-dimethoxy-12-N,N-dimethylaminoethylamino-pyridazino[4',5':3,4]pyrrolo[2,1-a]isoquinoline hydrochloride;

3,4-Dihydro-6,7-dimethoxy-12-hydrazino-pyridazino[4',5':3,4]pyrrolo[2,1-a]isoquinoline;

3,4-Dihydro-6,7-dimethoxy-12-dimethylamino-pyridazino[4',5':3,4]pyrrolo[2,1-a]isoquinoline hydrochloride;

3,4-Dihydro-6,7-dimethoxy-12-morpholino-pyridazino[4',5':3,4]pyrrolo[2,1-a]isoquinoline hydrochloride;

3,4-Dihydro-6,7-dimethoxy-pyridazino[4',5':3,4]pyrrolo[2,1-a]isoquinoline-12-acetonylhydrazone;

3,4-Dihydro-6,7-dimethoxy-12-anilino-pyridazino[4',5':3,4]pyrrolo[2,1-a]isoquinoline hydrochloride;

3,4-Dihydro-6,7-dimethoxy-12-methylamino-pyridazino[4',5':3,4]pyrrolo[2,1-a]isoquinoline hydrochloride;

3,4-Dihydro-6,7-dimethoxy-12-ethylamino-pyridazino[4',5':3,4]pyrrolo[2,1-a]isoquinoline hydrochloride;

3,4-Dihydro-6,7-dimethoxy-12-diethylamino-pyridazino[4',5':3,4]pyrrolo[2,1-a]isoquinoline hydrochloride;

3,4-Dihydro-6,7-dimethoxy-12-cyclopropylamino-pyridazino[4',5':3,4]pyrrolo[2,1-a]isoquinoline hydrochloride;

3,4-Dihydro-6,7-dimethoxy-12-isopropylamino-pyridazino[4',5':3,4]pyrrolo[2,1-a]isoquinoline hydrochloride;

3,4-Dihydro-6,7-dimethoxy-12-butylamino-pyridazino[4',5':3,4]pyrrolo[2,1-a]isoquinoline hydrochloride;

3,4-Dihydro-6,7-dimethoxy-12-N,N-dimethylhydrazino-pyridazino[4',5':3,4]pyrrolo[2,1-a]isoquinoline hydrochloride;

3,4-Dihydro-6,7-dimethoxy-12-(2-methoxyethyl)-amino-pyridazino[4',5':3,4]pyrrolo[2,1-a]isoquinoline hydrochloride;

3,4-Dihydro-6,7-dimethoxy-12-[2-(3,4-dimethoxyphenyl)ethyl]-amino-pyridazino[4',5':3,4]pyrrolo[2,1-a]isoquinoline hydrochloride;

3,4-Dihydro-6,7-dimethoxy-12-(3-aminopyrazolyl)pyridazino[4',5':3,4]pyrrolo[2,1-a]isoquinoline hydrochloride;

3,4-Dihydro-6,7-dimethoxy-12-cyclopentylamino-pyridazino[4',5':3,4]pyrrolo[2,1-a]isoquinoline hydrochloride;

3,4-Dihydro-6,7-dimethoxy-12-cyclohexylmethylamino-pyridazino[4',5':3,4]pyrrolo[2,1-a]isoquinoline hydrochloride;

3,4-Dihydro-6,7-dimethoxy-12-propargylamino-pyridazino[4',5':3,4]pyrrolo[2,1-a]isoquinoline hydrochloride;

3,4-Dihydro-6,7-dimethoxy-12-{2-[2-(1-methyl)-pyrrolidinyl]ethyl}-amino-pyridazino[4',5':3,4]pyrrolo[2,1-a]isoquinoline hydrochloride;

3,4-Dihydro-6,7-dimethoxy-12-[2-(1-piperidinyl)ethyl]-amino-pyridazino[4',5':3,4]pyrrolo[2,1-a]isoquinoline hydrochloride;

3,4-Dihydro-6,7-dimethoxy-12-pyrrolidinyl-pyridazino[4',5':3,4]pyrrolo[2,1-a]isoquinoline hydrochloride;

3,4-Dihydro-6,7-dimethoxy-12-n-propylamino-pyridazino[4',5':3,4]pyrrolo[2,1-a]isoquinoline hydrochloride;

12-Allylamino-3,4-dihydro-6,7-dimethoxy-pyridazino[4',5':3,4]pyrrolo[2,1-a]isoquinoline hydrochloride;

3,4-Dihydro-6,7-dimethoxy-12-[4-(2-methoxyphenyl)piperazinyl]-pyridazino[4',5':3,4]pyrrolo[2,1-a]isoquinoline hydrochloride;

3,4-Dihydro-6,7-dimethoxy-12-(3-dimethylaminopropyl)amino-pyridazino[4',5':3,4]pyrrolol[2,1-a]isoquinoline hydrochloride;

3,4-Dihydro-6,7-dimethoxy-12-[2-(1-morpholinyl)ethyl] amino-pyridazino[4',5':3,4]pyrrolo[2,1a]isoquinoline hydrochloride;

3,4-Dihydro-6,7-dimethoxy-12-n-pentylamino-pyridazino[4',5':3,4]pyrrolo[2,1-a]isoquinoline hydrochloride;

3,4-Dihydro-6,7-dimethoxy-12-cyclohexylamino-pyridazino[4',5':3,4]pyrrolo[2,1-a]isoquinoline hydrochloride;

3,4-Dihydro-6,7-dimethoxy-12-[4-(2-phenylethyl)piperazinyl]-pyridazino[4',5':3,4]pyrrolo[2,1-a]isoquinoline hydrochloride;

3,4-Dihydro-6,7-dimethoxy-12-furfurylamino-pyridazino[4',5':3,4]pyrrolo[2,1-a]isoquinoline hydrochloride;

3,4-Dihydro-6,7-dimethoxy-12-(3-methoxypropylamino)pyridazino[4',5':3,4]pyrrolo[2,1-a]isoquinoline hydrochloride;

3,4-Dihydro-6,7-dimethoxy-12-isopentylamino-pyridazino[4,'5':3,4]pyrrolo[2,1-a]isoquinoline hydrochloride;

3,4-Dihydro-6,7-dimethoxy-12-[2-(1-pyrrolidinyl)ethyl]-amino-pyridazino[4',5':3,4]pyrrolo[2,1-a]isoquinoline hydrochloride;

3,4-Dihydro-6,7-dimethoxy-12-(2-hydroxyethyl)-amino-pyridazino[4',5':3,4]pyrrolo[2,1-a]isoquinoline hydrochloride;

3,4-Dihydro-6,7-dimethoxy-12-(4-fluoroanilino)-pyridazino[4',5':3 4]pyrrolo[2,1-a]isoquinoline hydrochloride;

3,4-Dihydro-6,7-dimethoxy-12-[2-(4-pyridinyl)-ethyl]-amino-pyridazino[4',5':3,4]pyrrolo[2,1-a]isoquinoline hydrochloride;

3,4-Dihydro-6,7-dimethoxy-12-[2-(2-pyridinyl)-ethyl]-amino-pyridazino[4',5':3,4]pyrrolo[2,1-a]isoquinoline hydrochloride;

12-(4-Amino-1-benzyl-piperidinyl)-3,4-dihydro-6,7-dimethoxy-pyridazino[4',5':3,4]pyrrolo[2,1-a]isoquinoline hydrochloride;

3,4-dihydro-6,7-dimethoxy-12-[2-(3-thienyl)-ethyl]-amino-pyridazino[4',5':3,4]pyrrolo[2,1-a]isoquinoline hydrochloride;

3,4-Dihydro-6,7-dimethoxy-12-[2-[2-(1-methyl)-pyrrolyl] ethyl ]-amino-pyridazino[4',5':3,4]pyrrolo[2,1-a]isoquinoline hydrochloride;

3,4-Dihydro-6,7-dimethoxy-12-amino-pyridazino[4',5':3,4] pyrrolo[2,1-a]isoquinoline hydrochloride;

3,4-Dihydro-6,7-dimethoxy-12-[4-(2-phenylethyl)piperazinyl]pyridazino[4',5':3,4]pyrrolo[2,1-a]isoquinoline hydrochloride;

3,4-Dihydro-6,7-dimethoxy-12-isobutylamino-pyridazino[4',5':3,4]pyrrolo-[2,1-a]isoquinoline hydrochloride; and 3,4-Dihydro-6,7-dimethoxy-12-benzylamino-pyridazino[4',5':3,4]pyrrolo-[2,1-a]isoquinoline hydrochloride.

The new 12-amino-pyridazino[4',5':3,4]pyrrolo[2,1-a]isoquinolines of general formula (I) have valuable therapeutic properties both as bases and in the form of their salts. They show strong bonding to the muscarinic receptor; this is demonstrated by tests in which homogenized material from various parts of a rat's brain is incubated with tritium-N-methylscopolamine and the radioligands are displaced by adding the substance which is to be tested. The displacement constitutes a measure of the affinity of the substance for the muscarinic-cholinergic receptor. (Cf. M. Watson et al., Live Science, Volume 32, page 3001–3011 (1983) and R. Hammer et al., Nature, Volume 283, page 90–92 (1980)). Compounds of general formula (I) have also proved highly effective in tests for cardiotonic activity on isolated guinea pig auricles. In this test, spontaneously beating isolated auricles were used; the quantitatively measured positively inotropic activity is a measurement of the effect on contractility. The $EC_{50}$ is the quantity of active substance in mg/kg which brings about a 50% increase in contractility. (See R. Reichl, W. Traunecker, A. Engelhardt: Proceedings of the 12th meeting of the European Society for the study of Drug Toxicity. Uppsala June 1970 Excerpta Medica Int. Congr. Series Nr. 220-Isolierter Herzvorhof).

The compounds of general formula (I) and acid addition salts thereof are useful for the treatment of cardiac insufficiency and cerebral metabolic disorders and their use in this context comprises a further aspect of the invention.

According to a yet further aspect of the invention, therefore, we provide a pharmaceutical composition which comprises a compound of general formula (I), or a pharmaceutically acceptable acid addition salt thereof, together with a pharmaceutically acceptable carrier or excipient.

The compounds may be administered by both enteral and parenteral routes. The proposed dosage for oral use is 5 to 500, preferably 20 to 250 mg of active substance per dose, whilst the recommended dose for intravenous application is from 0.5 to 150, preferably from 5 to 50 mg per dose.

Suitable forms for administration include tablets, capsules, suppositories, solutions, syrups, emulsions, aerosols and dispersible powders. Suitable tablets may be prepared, for example, by mixing the active substance or substances with known adjuvants, for example inert diluents such as calcium carbonate, calcium phosphate or lactose, disintegrants such as corn starch or alginic acid, binders such as starch or gelatine, lubricants such as magnesium stearate or talc and/or agents for obtaining delayed release such as carboxypolymethylene, carboxymethylcellulose, cellulose acetate phthalate or polyvinyl acetate. The tablets may also consist of several layers.

Coated tablets may be prepared in the same way by coating cores produced analogously to the tablets with substances conventionally used for tablet coating, e.g. collidone or shellack, gum arabic, talc, titanium dioxide or sugar. In order to obtain delayed release or prevent intolerance, the core may also consist of several layers. Similarly, the tablet coating may consist of several layers in order to achieve delayed release, using the excipients given above for the tablets.

Syrups of the active substances or combinations of active substances according to the invention may additionally contain a sweetener such as saccharin, cyclamate, glycerine or sugar and a flavor-enhancing agent, e.g. a flavoring such as vanillin or orange extract. They may also contain suspension adjuvants or thickeners such as sodium carboxymethylcellulose, wetting agents,. e.g. condensation products of fatty alcohols with ethylene oxide, or preservatives such as p-hydroxybenzoates.

Solutions for injection may be prepared in conventional manner, e.g. with the addition of preservatives such as p-hydroxybenzoates or stabilizers such as alkali metal salts of ethylenediamine tetraacetic acid and may then be transferred into injection vials or ampoules.

Capsules containing the active substances or combinations of active substances may be prepared, for example, by mixing the active substances with inert vehicles such as lactose or sorbitol and encapsulating them in gelatine capsules.

Suitable suppositories may be prepared, for example, by mixing with carrier substances provided for this purpose, such as neutral fats or polyethylene glycol or derivatives thereof.

The following Examples serve to illustrate the invention more fully:

EXAMPLE 1

3,4-Dihydro-6,7-dimethoxy-12-N,N-dimethylaminoethyamino-pyridazino[4',4':3,4]pyrrolo[2,1-a]isoquinoline hydrochloride 3,4-Dihydro-6,7-dimethoxy-12-methylmercaptopyridazino[4',5':3,4]pyrrolo[2,1-a]isoquinoline (8 g) and 15 ml of (N,N-dimethylaminoethyl)-amine are boiled for 2 hours in 100 ml of dimethylacetamide. After cooling to ambient temperature, the orange-yellow solution is concentrated by evaporation in vacuo, the oily residue is taken up in methylene chloride, extracted with water and dried over sodium sulphate. After the solvent has been eliminated, the residue is purified over an $Al_2O_3$ column (neutral $Al_2O_3$, Messrs. Woelm, Activity Stage III, Eluent: methylene chloride/methanol (100:8)). The reaction product is dissolved in ethanol and precipitated in the form of the hydrochloride by the addition of ethanolichydrochloric acid.
Yield: 6.6 g (73% of theory); m.p.>250° C.

EXAMPLE 2

3,4-Dihydro-6,7-dimethoxy-12-hydrazino-pyridazino[4', 5':3,4]pyrrolo[2,1-a]isoquinoline 3,4-Dihydro-6,7-dimethoxy-12-methylmetcaptopyridazino[4',5':3,4]pyrrolo[2,1-a]isoquinoline (5 g) are heated to boiling for 2 hours in 200 ml of ethanol with 10 ml of hydrazine hydrate. After the reaction has ended, the reaction mixture is evaporated in vacuo, the residue is stirred with water, suction filtered and the filter residue is recrystallized from ethanol/ether. The title compound is obtained in a yield of 3.4 g (71% of theory);
M.p. 254°–257° C.

EXAMPLE 3

3,4-Dihydro-6 7-dimethoxy-12-dimethylamino-pyridazino[4',5':3,4]pyrrolo[2,1-a]isoquinoline hydrochloride 5 g of 3,4-Dihydro-6,7-dimethoxy-12-methylmercaptopyridazino[4',5':3,4]pyrrolo[2,1-a]isoquinoline are heated to boiling in 100 ml of dimethylformamide for 15 hours. After the reaction has ended the reaction mixture is concentrated by evaporation, the residue is suspended in methylene chloride and suction filtered. After the filter residue has been dissolved in hot methanol the base is converted into the hydrochloride and precipitated by the addition of ethanolic hydrochloric acid.
Yield of title compound: 3.6 g (72% of theory);
M.p. 264° C.

The following were obtained in a manner analogous to that of Example 3:

Starting from 3,4-dihydro-6,7-dimethoxy-12-methylmercaptopyridazino[4',5':3,4]pyrrolo2,1-a]isoquinoline, and by reaction with formamide: 3,4-dihydro-6,7-diemthoxy-12-amino-pyridazino[4',5':3,4]pyrrolo[2,1-a]isoquinoline hydrochloride, m.p. 271° C.

Starting from 3,4-dihydro-6,7-dimethoxy-12-methylmercaptopyridazino[4',5':3,4]pyrrolo[2,1-a]isoquinoline, and by reaction with methylformamide: 3,4-dihydro-6,7-dimethoxy-12-methylamino-pyridazino[4',5':3,4]pyrrolo[2, 1-a]isoquinoline hydrochloride, m.p. 260°–265° C.

EXAMPLE 4

3,4-Dihydro-6,7-dimethoxy-12-dimethylamino-pyridazino[4',5':3,4]pyrrolo[2,1-a]isoquinoline-hydrochloride 3,4-Dihydro-6,7-dimethoxy-12-methylmercaptopyridazino[4',5':3,4]pyrrolo[2,1-a]isoquinoline (5 g) are heated to 120° C. in 50 ml of dimethylacetamide with 20 ml of dimethylamine for 10 hours in an autoclave. After the reaction has ended, the solvent is eliminated in vacuo, the residue is purified on silica gel (eluant: methylene chloride/methanol (100:10)), the hydrochloride is formed and crystallized from methanol.
Yield: 3.1 g (63% of theory); m.p. 264° C.

The following compounds were also prepared using the above procedure:

3,4-Dihydro-6,7-dimethoxy-12-methylamino-pyridazino [4',5':3,4]pyrrolo[2,1-a]isoquinoline hydrochloride.
Yield: 3.2 g (67% of theory); m.p.>250° C.

3,4-Dihydro-6,7-dimethoxy-12-ethylamino-pyridazino [4',5':3,4]pyrrolo[2,1-a]isoquinoline hydrochloride.
Yield: 3.1 g (63% of theory); m.p. 273° C.

3,4-Dihydro-6,7-dimethoxy-12-diethylamino-pyridazino [4',5':3,4]pyrrolo[2,1-a]isoquinoline hydrochloride.
Yield: 3.4 g (67% of theory); m.p. 276° C.

3,4-Dihydro-6,7-dimethoxy-12-cycloptopylamino-pyridazino[4',5':3,4]pyrrolo[2,1-a]isoquinoline hydrochloride.
Yield: 2.4 g (46% of theory); m.p. >260° C.

EXAMPLE 5

3,4-Dihydro-6,7-dimethoxy-12-morpholino-pyridazino [4',5':3,4]pyrrolo[2,1-a]isoquinoline hydrochloride 5 g of 3,4-Dihydro-6,7-dimethoxy-12-methylmercaptopyridazino-[4',5':3,4]pyrrolo[2,1-a]isoquinoline (5 g) and 20 ml of morpholine are heated to boiling in 100 ml of dimethylacetamide for 1.5 hours. After the reaction has ended the reaction mixture is concentrated by evaporation in vacuo, the residue is triturated with methylene chloride and suction filtered. The reaction product is dissolved in a mixture of methylene chloride and methanol, converted into the hydrochloride by the addition of ethanolic hydrochloric acid and crystallized. The yield of title compound is 3.5 g (63% of theory); m.p. 267° C.

The following were prepared by a manner analogous to the method described above:

3,4-Dihydro-6,7-dimethoxy-12-isopropylamino-pyridazino[4',5':3,4]pyrrolo[2,1-a]isoquinoline hydrochloride
Yield: 3.0 g (57% of theory); m.p 238° C.

3,4-Dihydro-6,7-dimethoxy-12-butylamino-pyridazino[4',5':3,4]pyrrolo[2,1-a]isoquinoline hydrochloride
Yield: 4.2 g (78% of theory); m.p 257° C.

3,4-Dihydro-6,7-dimethoxy-12-N,N-dimethylhydrazino-pyridazino[4',5':3,4]pyrrolo[2,1-a]isoquinoline hydrochloride.
Yield: 4.5 g (87% of theory); m.p >265° C.

3,4-Dihydro-6,7-dimethoxy-12-(2-methoxyethyl)-amino-pyridazino[4',5':3,4]pyrrolo[2,1-a]isoquinoline hydrochloride.
Yield: 3.6 g (67% of theory); m.p 252° C.

3,4-Dihydro-6,7-dimethoxy-12-[2-(3,4-dimethoxyphenyl)ethyl]-amino-pyridazino[4',5':3,4]pyrrolo[2,1-a]isoquinoline hydrochloride.
Yield: 5.5 g (78% of theory); m.p 257° C.

3,4-Dihydro-6,7-dimethoxy-12- (3-aminopyrazolyl)pyridazino[4',5':3,4]pyrrolo[2,1-a]isoquinoline hydrochloride.
Yield: 4.1 g (68% of theory); m.p >260° C.

3,4-Dihydro-6,7-dimethoxy-12-cyclopentylamino-pyridazino[4',5':3,4]pyrrolo[2,1-a]isoquinoline hydrochloride.
Yield: 3.1 g (56% of theory); m.p 265° C.

3,4-Dihydro-6,7-dimethoxy-12-cyclohexylmethylamino-pyridazino[4',5':3,4]pyrrolo[2,1-a]isoquinoline hydrochloride.
Yield: 5.2 g (87% of theory); m.p 262° C.

3,4-Dihydro-6,7-dimethoxy-12-propargylamino-pyridazino[4',5':3,4]pyrrolo[2,1-a]isoquinoline hydrochloride.
Yield: 3.7 g (73% of theory); m.p 247° C.

3,4-Dihydro-6,7-dimethoxy-12-{2-[2-(1-methyl)-pyrrolidinyl]ethyl}-amino-pyridazino[4',5':3,4]pyrrolo[2,1-a]isoquinoline hydrochloride.
Yield: 4.3 g (69% of theory); m.p 256°–258° C.

3,4-Dihydro-6,7-dimethoxy-12-[2-(1-piperidinyl)ethyl]-amino-pyridazino[4',5':3,4]pyrrolo[2,1-a]isoquinoline hydrochloride.
Yield: 3.3 g (53% of theory); m.p 248°–251° C.

3,4-Dihydro-6,7-dimethoxy-12-pyrrolidinyl-pyridazino[4',5':3,4]pyrrolo[2,1-a]isoquinoline hydrochloride.
Yield: 3.1 g (59% of theory); m.p 277°–278° C.

3,4-Dihydro-6,7-dimethoxy-12-n-propylamino-pyridazino[4',5':3,4]pyrrolo[2,1-a]isoquinoline hydrochloride.
Yield: 3.7 g (72% of theory); m.p 258° C.

12-Allylamino-3,4-dihydro-6,7-dimethoxy-pyridazino[4',5':3,4]pyrrolo[2,1-a]isoquinoline hydrochloride.
Yoeld: 2.7 g (53% of theory); m.p 260°–263° C.

3,4-Dihydro-6,7-dimethoxy-12-[4-(2-methoxyphenyl)-piperazinyl]pyridazino[4',5':3,4]pyrrolo[2,1-a]isoquinoline hydrochloride.
Yield: 4.8 g (66% of theory); m.p 250°–252° C.

3,4-Dihydro-6,7-dimethoxy-12-(3-dimethylaminopropyl)amino-pyridazino[4',5':3,4]pyrrolo[2,1-a]isoquinoline hydrochloride.
Yield: 2.4 g (43% of theory); m.p>250° C.

3,4-Dihydro-6,7-dimethoxy-12-[2-(1-morpholinyl)ethyl]-amino-pyridazino[4',5':3,4]pyrrolo[2,1-a]isoquinoline hydrochloride.
Yield: 3.4 g (54% of theory); m.p >260° C.

3,4-Dihydro-6,7-dimethoxy-12-n-pentylamino-pyridazino[4',5':3,4]pyrrolo[2,1-a]isoquinoline hydrochloride
Yield: 4.9 g (87% of theory); m.p 259°–261° C.

3,4-Dihydro-6,7-dimethoxy-12-cyclohexylamino-pyridazino[4',5':3,4]pyrrolo[2,1-a]isoquinoline hydrochloride
Yield: 3.8 g (66% of theory); m.p 253° C.

3,4-Dihydro-6,7-dimethoxy-12-[4-(2-phenylethyl)piperazinyl]-pyridazino[4',5':3,4]pyrrolo[2,1-a]isoquinoline hydrochloride.
Yield: 3.8 g (53% of theory); m.p 264° C.

3,4-Dihydro-6,7-dimethoxy-12-furfurylamino-pyridazino[4',5':3,4]pyrrolo[2,1-a]isoquinoline hydrochloride.
Yield: 3.2 g (56% of theory); m.p 243°–246° C.

3,4-Dihydro-6,7-dimethoxy-12-(3-methoxypropylamino)pyridazino[4',5':3,4]pyrrolo[2,1-a]isoquinoline hydrochloride.
Yield: 3.6 g (65% of theory); m.p >250° C.

3,4-Dihydro-6,7-dimethoxy-12-isopentylamino-pyridazino[4',5':3,4]pyrrolo[2,1-a]isoquinoline hydrochloride.
Yield: 3.2 g (58% of theory); m.p 259° C.

3,4-Dihydro-6,7-dimethoxy-12-[2-(1-pyrrolidinyl)ethyl]-amino-pyridazino[4',5':3,4]pyrrolo[2,1-a]isoquinoline hydrochloride.
Yield: 3.3 g (55% of theory); m.p >260° C.

3,4-Dihydro-6,7-dimethoxy-12-(2-hydroxyethyl)-amino-pyridazino[4',5':3,4]pyrrolo[2,1-a]isoquinoline hydrochloride.
Yield: 4.2 g (80% of theory); m.p 259° C.

EXAMPLE 6

3,4-Dihydro-6,7-dimethoxy-pyridazino[4',5':3,4]pyrrolo[2,1-a]isoquinoline-acetonylhydrazone 3,4-Dihydro-6,7-dimethoxy-12-hydrazino-pyridazino[4',5':3,4]pyrrolo[2,1-a]isoquinoline (1 g) are dissolved in 50 ml of acetone and heated to boiling for half an hour. The mixture is evaporated in vacuo and the crystals which are precipitated in the cold are suction filtered.
Yield: 5.1 g (95% of theory); m.p. 173°–175° C.

EXAMPLE 7

3,4-Dihydro-6,7-dimethoxy-12-anilino-pyridazino[4',5':3,4]-pyrrolo[2,1-a]isoquinoline-hydrochloride 3,4-Dihydro-6,7-dimethoxy-12-methylmetcaptopyridazino[4',5':3,4]pyrrolo[2,1-a]isoquinoline (5 g) are heated to boiling in 50 ml of aniline under a protective nitrogen atmosphere for 6 hours. Excess aniline is eliminated in vacuo, the residue is triturated with methylene chloride, suction filtered and recrystallized from methanol/methylene chloride.
Yield: 3.0 g (53% of theory); m.p. >250° C.

The following were prepared in an analogous manner:
3,4-Dihydro-6,7-dimethoxy-12-(4-fluoroanilino)-pyridazino[4',5':3,4]pyrrolo[2,1-a]isoquinoline hydrochloride.
Yield: 4.0 g (67% of theory); m.p.>270° C.

3,4-Dihydro-6,7-dimethoxy-12-[2-(4-pyridinyl)-ethyl]-amino-pyridazino-[4',5':3,4]pyrrolo[2,1-a]isoquinoline hydrochloride.
Yield: 4.1 g (70% of theory); m.p. 260° C.

3,4-Dihydro-6,7-dimethoxy-12-[2-(2-pyridinyl)-ethyl]-amino-pyridazino-[4',5':3,4]pyrrolo[2,1-a]isoquinoline hydrochloride.
Yield: 3.7 g (62% of theory); m.p. >260° C.

12-(4-Amino-1-benzyl-piperidinyl)-3,4-dihydro-6,7-dimethoxy-pyridazino[4',5':3,4 ]pyrrolo[2,1-a]isoquinoline hydrochloride.

Yield: 3.9 g (56% of theory); m.p. >250° C.

3,4-dihydro-6,7-dimethoxy-12-[2-(3-thienyl)-ethyl]-amino-pyridazino[4',4':3,4]pyrrolo[2,1-a]isoquinoline hydrochloride.

Yield: 4.0 g (65% of theory); m.p. >280° C.

3,4-Dihydro-6,7-dimethoxy-12-[2-[3-(1-methyl)-pyrrolyl]ethyl]-amino-pyridazino-[4',5':3,4]pyrrolo[2,1-a]isoquinoline hydrochloride.

Yield: 3.6 g (61% of theory); m.p. 256°–258° C.

3,4-Dihydro-6,7-dimethoxy-12-[2-(1-piperidinyl)-ethyl]-amino-pyridazino-[4',5':3,4 ]pyrrolo[2,1-a]isoquinoline hydrochloride.

Yield: 3.6 g ( 58% of theory); m.p. 250° C.

3,4-Dihydro-6,7-dimethoxy-12-isobutylamino-pyridazino[4',5':3,4]pyrrolo[2,1-a]isoquinoline hydrochloride. M.p. 250° C.

3,4-Dihydro-6,7-dimethoxy-12-benzylamino-pyridazino [4',5':3,4]pyrrolo[2,1-a]isoquinoline hydrochloride. M.p. 257° C.

The preparation of some starting compounds will now be described, taking as an example 3,4-dihydro-6,7-dimethoxy-12-methylmercapto-pyridazino[4',5':3,4 ]pyrrolo[2,1-a]isoquinoline.

a) 3,4,11,12-Tetrahydro-6,7-dimethoxypyridazino[4',5':3, 4]pyrrolo[2,1-a]isoquinolin-12-one Ethyl 1-formyl-5,6-dihydro-8,9-dimethoxypyrrolo[2,1-a] isoquinolin-2-carboxylate (8.25 g) and 7 ml of hydrazine hydrate are stirred in 40 ml of boiling pyridine for 3 hours. After cooling, the crystalline precipitate is suction filtered and any pyridine adhering is removed by washing with methanol. The product obtained is analytically pure and is used for the next stage without further purification.

Yield: 7.1 g (95.4% of theory); m.p. >285° C.

b) 3,4,11,12-Tetrahydro-6,7-dimethoxy-pyridazino[4', 5':3,4]pyrrolo[2,1-a]isoquinolin-12-thione Phosphorous pentasulfide (302 g) are quickly added in batches to a suspension of 404 g of 3,4,11,12-tetrahydro-6, 7-dimethoxy-pyridazino[4',5':3,4]pyrrol[2,1-a]isoquinolin-12-one in 2.81 of pyridine, with stirring at ambient temperature. As the temperature rises slightly to a maximum of 60° C., a yellow solution is formed from which orange-yellow crystals are soon precipitated. The reaction mixture is refluxed for about 4 hours, allowed to cool to ambient temperature and then the crystals are suction filtered. They are digested in a mixture of 1 l of water and 200 ml of ethanol and, after suction filtering, dried in vacuo at 60° C. The product is processed further without any more purification. For analysis a sample is crystallized from ethanol/methylene chloride.

Yield: 392 g (92% of theory); m.p. 294° C.

c) 3,4-Dihydro-6,7-dimethoxy-12-methylmercapto-pyridazino[4',5':3,4]pyrrolo[2,1-a]isoquinoline A suspension of 100 g of 3,4,11,12-tetrahydro-6,7-dimethoxy-pyridazino[4',5':3,4]pyrrolo[2,1-a]isoquinolin-12-thionein 600 ml of dimethylacetamide is mixed with 20 ml of methyliodide at ambient temperature with stirring. After the mixture has been stirred for about 20 minutes at ambient temperature, an orangy-yellow solution is formed, out of which orange crystals are precipitated after a further 50 minutes. The mixture is stirred for another hour, the crystals are suction filtered and was held with methylene chloride. A second fraction is obtained from the mother liquor after evaporation and trituration with methylene chloride. The product obtained is pure according to NMR spectroscopy and is worked up without any further purification. A sample was recrystallized from dimethylacetamide for analysis.

Yield: 99.8 g (96% of theory); m.p. 254° C.

PHARMACY EXAMPLES a) Coated tablets

| 1 tablet core contains: | |
|---|---|
| Active substance of formula (I) according to the invention | 150.0 mg |
| Lactose | 50.0 mg |
| Corn starch | 22.0 mg |
| Gelatine | 2.0 mg |
| Magnesium stearate | 1.0 mg |
| | 225.0 mg |

Preparation

A mixture of the active substance with lactose and corn starch is granulated with a 10% aqueous gelatine solution through a screen having a mesh size of 1 mm, then dried at 40° C. and rubbed through another screen. The granulate obtained is mixed with magnesium sterate and compressed. The resulting cores are coated in the usual way with a coating produced by an aqueous suspension of sugar, titanium dioxide, talc and gum arabic. The finished coated tables are polished with bees wax.

Finished weight of coated tablet: 200 mg.

b) Tablets

| Active substance of formula (I) according to the invention | 100.0 mg |
|---|---|
| Lactose | 40.0 mg |
| Corn starch | 44.0 mg |
| Soluble starch | 5.0 mg |
| Magnesium stearate | 1.0 mg |
| | 190.0 mg |

Preparation

The active substance and magnesium stearate are granulated with an aqueous solution of the soluble starch, the granulate is dried and intimately mixed with lactose and corn starch. The mixture is then compressed to form tablets weighing 100 mg each containing 10 mg of active substance.

c) Suppositories

| 1 suppository contains: | |
|---|---|
| Active substance of formula (I) according to the invention | 120.0 mg |
| Suppository mass | 1680.0 mg |

· Preparation

The finely powdered substance is stirred into the molten suppository mass which has been cooled to 40° C. with an immersion homogenizer. The mass is poured into slightly chilled molds at 35° C.

d) Ampoules

| Composition: | |
|---|---|
| Active substance of formula (I) according to the invention | 50.0 parts by weight |
| Sodium pyrosulfite | 1.0 parts by weight |

-continued

| Composition: | |
|---|---|
| Disodium salt of ethylene-diaminetetraacetic acid | 0.5 parts by weight |
| Sodium chloride | 8.5 parts by weight |
| doubly distilled water ad | 1000.0 parts by weight |

Preparation

The substance and excipients are dissolved in a sufficient quantity of water and made up to the desired concentration with the required quantity of water. The solution is filtered and transferred into 1 ml ampoules under aseptic conditions. Finally the ampoules are sterilized and sealed.

Each ampoule contains 50.0 mg of active substance.

We claim:

1. A compound of the formula

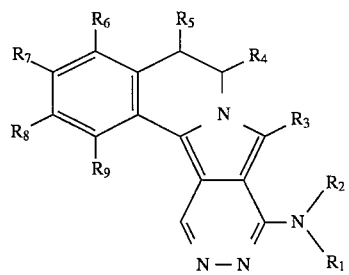

or a pharmaceutically acceptable acid addition salt thereof, wherein, $R_1$ and $R_2$ are the same or different and each is hydrogen; $C_{3-7}$ cycloalkyl; phenyl; phenyl mono- or disubstituted by halogen or methoxy; straight or branched chain, saturated, or unsaturated $C_{1-5}$ alkyl which may be substituted by hydroxy, $C_{1-4}$ alkoxy, halogen, amino, $C_{1-2}$ alkylamino-, $C_{1-2}$ dialkylamino, $C_{2-4}$ acylamino, $C_{3-7}$ or phenyl; furyl; or, thienyl;

or, $R_1$ and $R_2$ together with the nitrogen atom to which they are attached form a 4-piperazinyl, 1-morpholino, 1-pyrrolidinyl or 1-piperidinyl ring which is unsubstituted or substituted by phenyl $C_{1-4}$ alkyl, wherein the phenyl is unsubstituted or substituted by halogen or methoxy;

with the proviso that, when $R_1$ is hydrogen, $R_2$ may additionally be amino, $C_{1-2}$ dialkylamino, acetonylamino, $C_{2-3}$ acylamino, $C_{1-3}$ alkylsulphonyl or $C_{1-3}$ alkoxycarbonyl;

$R_3$, $R_4$ and $R_5$ may be the same or different and each is hydrogen or $C_{1-4}$ alkyl;

$R_7$ and $R_8$ may be the same or different and each is hydroxy, $C_{1-4}$ alkoxy or $C_{1-4}$ alkylthio, and $R_6$ and $R_9$ may be the same or different and each is hydrogen, hydroxy, $C_{1-4}$ alkoxy, $C_{1-4}$ alkylthio, or a group

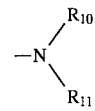

wherein $R_{10}$ is hydrogen or $C_{1-4}$ alkyl and $R_{11}$ is hydrogen or $C_{1-4}$ alkyl wherein any such alkyl group may be unsubstituted or substituted by hydroxy, methoxy or furfuryl.

2. A compound of formula (I), as claimed in claim 1, wherein $R_1$ and $R_2$, which may be the same or different, are each hydrogen, or straight- or branched-chain $C_{1-5}$ alkyl or $R_1$ is hydrogen and $R_2$ is amino, methylamino, dimethylamino, dimethylamino-$C_{1-4}$ alkyl, methoxy-$C_{1-4}$alkyl, cyclopropyl, cyclopentyl, cyclohexyl, cyclohexylmethyl, phenyl which is unsubstituted or mono- or disubstituted by methoxy, or p-halophenyl the phenyl moiety of which is optionally additionally mono- or disubstituted by methoxy, or $R_1$ and $R_2$ together with the nitrogen atom to which they are attached form a morpholino ring or a piperazine ring and $R_7$ and $R_8$ are each methoxy.

3. 3,4-Dihydro-6,7-dimethoxy-12-benzylamino-pyridazino[4',5':3,4]pyrrolo[2,1-a]isoquinoline, or a pharmaceutically acceptable salt thereof.

4. 3,4-Dihydro-6,7-dimethoxy-12-cyclohexylmethylamino-pyridazino[4',5':3,4]pyrrolo[2,1-a]isoquinoline, or a pharmaceutically acceptable salt thereof.

5. 3,4-Dihydro-6,7-dimethoxy-12-[4-(2-methoxyphenyl)piperazinyl]-pyridazino[4',5':3,4 ]pyrrolo[2,1-a]isoquinoline, or a pharmaceutically acceptable salt thereof.

6. 3,4-Dihydro-6,7-dimethoxy-12-[2-(3-thienyl)-ethyl]-aminopyridazino[4',5':3,4]pyrrolo[2,1-a]isoquinoline, or a pharmaceutically acceptable salt thereof.

7. A pharmaceutical composition which comprises a compound as claimed in claims 1, 2, 3, 4, 5 or 6 together with a pharmaceutically acceptable carrier or excipient.

8. A method of treating cardiac insufficiency which comprises administering to a subject suffering from the same a cardiotonic amount of a compound of formula (I), as claimed in claims 1, 2, 3, 4, 5 or 6 or a pharmaceutically acceptable acid addition salt thereof.

* * * * *